Dec. 17, 1974 G. NOBBIO Plant Pat. 3,663
PERPETUAL FLOWERING CARNATION PLANT
Filed Dec. 27, 1973
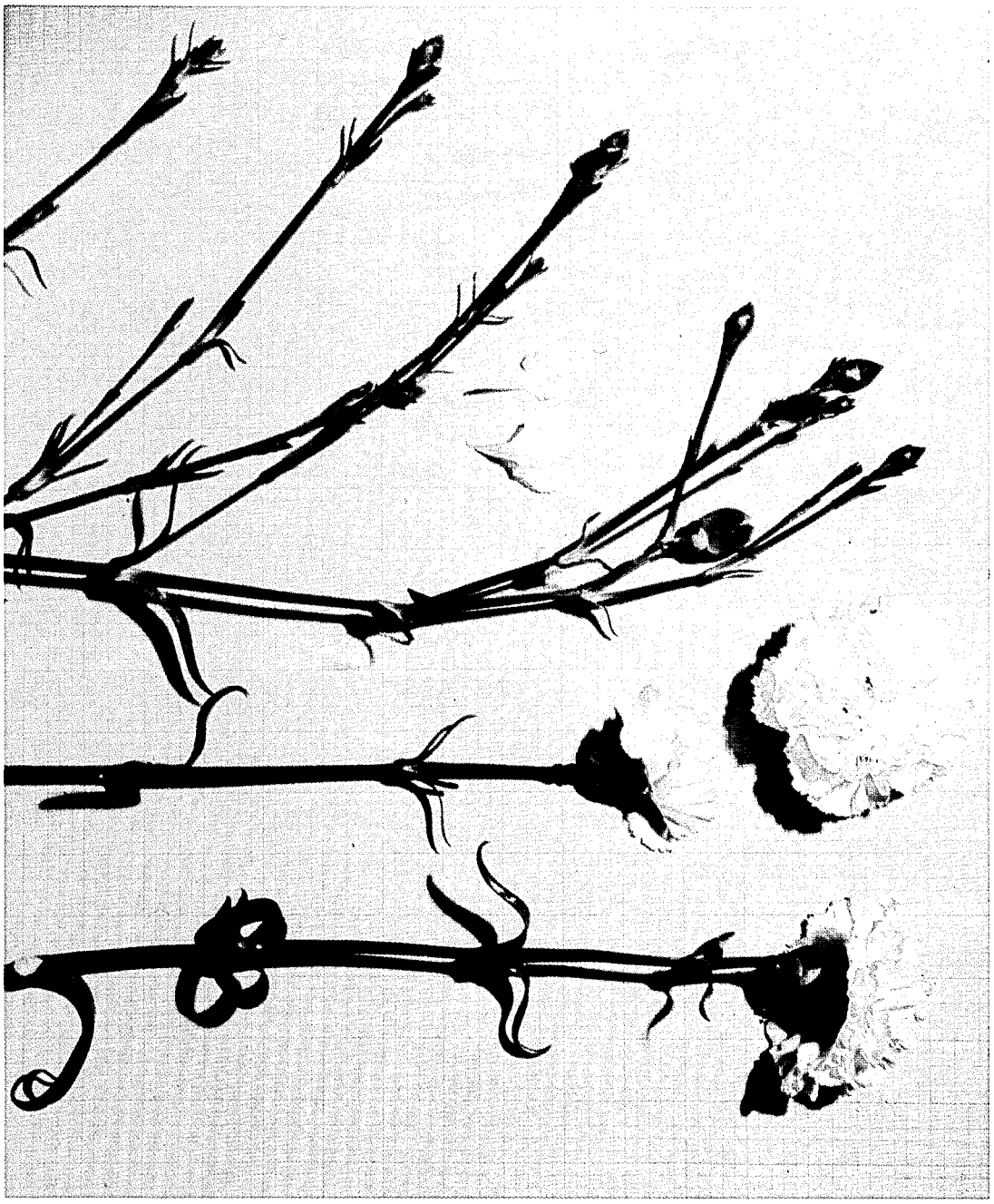

United States Patent Office

Plant Pat. 3,663
Patented Dec. 17, 1974

3,663
PERPETUAL FLOWERING CARNATION PLANT

Giacomo Nobbio, Duca degli Abruzzi n, 85,
San Remo, Italy

Filed Dec. 27, 1973, Ser. No. 428,893
Claims priority, application Italy May 29, 1973, 50,291/73
Int. Cl. A01h *5/00*
U.S. Cl. Plt.—70 1 Claim

ABSTRACT OF THE DISCLOSURE

A variety of perpetual flowering carnation with slender growth and having primrose yellow flowers with shades of chartreuse green.

BACKGROUND OF THE INVENTION

Flower growers have sought new varieties of flowers in order to follow the trends of the international cut flower market and to retain consumer interest with new varieties of cut flowers. In this way, it has been possible to obtain more competitive prices and to improve the efficiency of both the cultivation and the sale of cut flowers.

Thus, the present applicant has sought new varieties of flowers, and more particularly carnations. In the course of his research, he found that one of the plants, of a variety he had previously obtained, tended to have primrose yellow flowers—a color that is much appreciated on the market—instead of the original sulphur yellow flowers.

He therefore attempted to extend his color to the whole of the corolla and to make it stable, in order to create a new variety of flower having such desirable characteristics. These results were achieved in the plant which is the subject of the present invention.

DESCRIPTION OF THE INVENTION

The new variety which is the subject of the present invention differs from the plant "Alice," from which it originated, as well as from all other varieties of its class, and constitutes a noticeable improvement thereover.

It may be reproduced easily and propagated in any number of specimens, all of them having the properties of the original plant, by means of one of the development methods of plant propagation used in flower cultivation. More particularly, this can be done by taking cuttings from one of the lateral buds, or from another part of the plant according to the present invention, or from plants derived from it by vegetative means, and then planting them in choice soil conditions until an adult plant, suitable for cut flower production, is obtained.

By repeating the reproduction and propagation of the plant by this method, it has been ascertained that all the distinctive characteristics of the plant which is the subject of the present invention are transmitted in a constant and absolutely faithful manner to all the specimens obtained so far, so that populations of plants with perfectly homogeneous and stable characteristics have been formed.

The properties which distinguish the object of the present invention from other varieties of its class, and permit its identification, are listed in the following description by way of example alone and without any limitations. The description is based on a set of plants cultivated over a period of eleven months in natural soil—in the open air, and in glass houses—in a sunny spot on a hill in San Remo, Italy. The plants are described in the month of April.

Reference should always be made to these climatic and seasonal conditions in any comparison of this variety made as a function of the present description. Any possible differences which, as a result of different conditions of climate, soil or method of cultivation, may be encountered between certain features of the plant and the corresponding ones of the description must be considered normal, and should not modify the essence of the present invention—at least, so long as it is possible to identify the plant by means of the collection of features given in the description hereinbelow—by repeating the cultivation under the same conditions as those of the plants described.

In the description, the colors have been named according to the tables of the "Horticultural Color Chart" by Robert F. Wilson (indicated in the text by the initials HCC) except in those cases in which the colors were absent from the tables or where its indication was sufficiently clear in common parlance.

Classification: Botanical and commercial—perpetual flowering hybrid of the class of plants having a whole calyx.

Stock: "Sport" (bud mutation) of the "Alice" variety.

PLANT

Growth: Very vigorous plant, straight, slender, vertical growth, voluminous, dense and compact, bushy. Numerous flower-bearing stems only slightly divergent from the axis of the plant, starting only a little above the level of the earth.

Average height: 100–120 cm. from the soil level for fully developed plants cultivated as described above.

Roots: Numerous, well developed, thin or average thickness, slightly ramified, that dig deep into earth, length 15–20 cm., average diameter at the collar 2–4 mm. Few root hairs; color light yellow.

Main stem: Generally short between the collar and the first ramification, then longer, generally thick, articulated in one to three internodes of 1–1.5 cm. average length, with nodes ring-shaped standing out only slightly from the stem.

*Average Size.*—Length 20–30 mm. from the collar to the first ramification, followed by another segment of 80–100 mm. on which are inserted the flower branches. Average diameter at the collar 14–18 mm.

*Color.*—Nut brown.

Flower branches: Numerous, on average 6–10 starting from the main stem or from the base of other flower branches, at intervals of average length, in various stages of development.

*Shape.*—Almost cylindrical, robust, thick, diameter increasing from the base to a point about midway along length, then decreasing towards the tip of the stems, articulated in internodes of varying length, straight or not very sinuous, sometimes making an angle at the nodes.

*Average Size.*—Length 90–110 cm., diameter at the base 4–6 mm., midway along the branch 6–8 mm., and under the flower 3–4 mm.

Internodes: Numerous, on average 18–20 on the flower branches.

*Shape.*—Thick, almost cylindrical, slightly ventricose towards the nodes in the internodes towards the base; almost cylindrical or slightly conical due to graduated, club-shaped swelling towards the lower node, with longitudinal ribs and flats in the middle and higher internodes of the branch.

*Average Size.*—Variable according to the stage of development and the position on the branch, as a general average: length: first internode from the base 15–20 mm.; second internode 20–25 mm.; third 30–40 mm.; fourth 35–45 mm.; fifth 40–50 mm.; sixth 40–50 mm.; seventh 45–55 mm.; eighth 45–55 mm.; ninth 45–55 mm.; tenth 50–60 mm.; eleventh 60–70 mm.; twelfth 65–75 mm.; thirteenth 65–75 mm.; fourteenth 70–80 mm.; fifteenth 80–

90 mm.; sixteenth 100–110 mm.; seventeenth 100–110 mm.; eighteenth 70–80 mm.; nineteenth 35–45 mm.; twentieth 20–30 mm.; length of floral peduncle 10–15 mm.

*Diameters.*—At the base 4–6 mm.; mid-stem 6–8 mm.; under the flower 3–4 mm.

*Bark.*—Thick, smooth, hairless, pruinose, opaque with satiny lines.

*Color.*—Basic color close to spinach green (HCC page 187, shade 0960–0960/1,2,3) with varying shades; on the lower half of the internodes and on the nodes color pod green (HCC, page 120, shade 061/1,2) with lines of cerous cuticle color carnation green (HCC, page 194, shade 00058/2,3).

*Consistency.*—Thick, sturdy, almost woody.

Leaves: Large and abundant, inserted in opposing pairs on all the nodes.

*Shape.*—Ensiform lamina, slightly lanceolate with smooth edges and a sharp tip, carinated in a wide V-shape on the leaves towards the base, flatter or slightly concave on the upper face of the middle and higher leaves. Well marked veins, differentiated and standing out on the lower face, sometimes having sharp edges on the lowest leaves.

*Average Size.*—Lowest leaves, length 100–130 mm., width 7–12 mm.; middle and upper leaves, length 80–130 mm., width 13–15 mm.

*Color.*—Between spinach green (HCC, page 187, shades 0960–0960/1) and sage green (HCC, page 198, shade 000861) covered with strips of cerous cuticle, color Sung green (HCC, page 195, shade 000658/3).

*Surface.*—Smooth, hairless, slightly granulous, opaque.

*Consistency.*—Thick, fleshy, rigid, resistant.

*Bearing.*—Lower leaves downcurled in a more or less wide curve or bent at the base. Middle and upper leaves averagely divergent from the stem with the tip downcurved or slightly rolled in a spiral or circle.

*Foliar Sheath.*—Shaped from the base of the leaves grouped round the node and at the base of the upper internode for a distance of 10–15 mm.

Lateral shoots: Averagely numerous, more frequent at the base of the branches, with a tendency to grow into flower-bearing branches. The shoots inserted on the upper half of the branches tend to grow into secondary flower branches bearing small flower buds, diverging from the main branch and articulated in long, thin internodes. Intermediary shoots formed by 6–8 pairs of leaves inserted opposite each other along the axis of the shoot at average intervals.

*Average Size.*—Length varies according to stage of development. On average 120–180 mm.

FLOWER

Bearing: Main flower erect, terminal on the branch straight or slightly inclined, accompanied by 6–10 secondary buds carried by long lateral stems inserted on the highest nodes of the branch, which in turn are ramified with secondary stems frequently longer than the main flower.

Closed flower bud: Rounded egg-shape, almost cylindrical, with a hemispherical base having an obtuse or averagely sharp point. Opening of the bud pointed.

*Average Size.*—At the base of the sepals, length 25–30 mm., diameter 16–20 mm.

Calyx: Of the type generally closed, in the shape of a conical cup, averagely funnel-shaped towards the top with the sepal tips adhering to the open corolla petals.

*Average Size.*—With the corolla open: length 28–32 mm., diameter 20–25 mm.

*Sepals.*—5–6 in number, generally 6, fused together into a conical tube for about three quarters of their length, culminating in regular triangular points with squamose edges and forming a bulge at their base. The back of the sepals is longitudinally convex. Marked junction of the sepals.

*Color.*—Exterior—basic color pea green (HCC, page 120, shade 61–61/1) with varying shades, spinach green (HCC, page 187, shades 0960–0960/1) in the upper part, with fine longitudinal lines of the same color as the base. Slight tints of ivy green (HCC, page 200, shade 0001060/3) on the tips of the sepals. Inner face—pea green (HCC, page 120, shades 61–61/1).

*Surface.*—Outer side—smooth, hairless, pruinose, opaque. Inner side—smooth, hairless, luminous, waxy.

*Consistency.*—Thick, fleshy, leathery, resistant.

Calyx: Generally composed of 4 cordiform bracts, squamose on the edges arranged around the base of the calyx in opposite pairs, imbricated. Points of the bracts triangular, differentiated.

*Average Size.*—Outer bracts—length 9–11 mm., width 13–15 mm.; inner bracts—length 12–14 mm., width 18–20 mm.

*Color.*—Basic color pea green (HCC, page 120, shades 61/2,3), tinged with spinach green (HCC, page 187, shade 0960) at the base, with extensive triangular marks of a color close to ivy green (HCC, page 200, shade 0001060/3) on the tips of the bracts.

Open corolla: Large, double, with a regular outline, slightly scalloped and delicately indented, with the petals falling back a little onto the calyx. Guard petals well developed, undulating and folded down their length. Central petals free, erect, longitudinally folded and curly, wel developed. Center of the flower full, averagely raised, continuing into the outer petals. Profile of the flower fan-shaped lowered towards the calyx.

*Average Size.*—Average diameter, corolla open 80–90 mm. Length of the flowers from the base of the receptacle to the tip of the petals 55–65 mm.

*General Color.*—Primrose yellow (HCC, page 65, shade 601/1,2) with tones of Chartreuse green (HCC, page 90, shade 663/1,2,3) and a few longitudinal traces of white towards the edge of a few petals.

*Petals.*—Numerous, on average 60–70, and a few petalloid stamens in the middle of the flower.

*Shape.*—Outer petals — lamina of average to large size, triangular, rounded towards the outside or transversely elliptical, with the lateral edges converging on the claw of average length. Outer edge undulating and delicately scalloped with very short, rounded teeth. Claw of average length and average width, showing some longitudinal ribbing. Inner petals — averagely rounded, or irregularly rounded, triangular lamina, undulating and curly, often folded down the middle of its length. Outer edge undulating and finely scalloped with a few notches. Lateral edges smooth, even curly. Average sized claw, thin with ventral veins.

*Average Size.*—Outer petals—lamina: length 28–30 mm., width 32–38 mm.; claw: length 28–30 mm., width 1–8 mm.; inner petals—lamina: length 24–28 mm., width 20–25 mm.; claw: length 24–26 mm., width 1–6 mm.

*Color.* — Upper face — between Primrose yellow (HCC, page 65, shade 601/1,2) and Chartreuse green (HCC, page 90, shade 663/1,2,3), with longitudinal triangular streaks towards the edge with shades of white on a few petals. Lower face — the same colors as on the upper face, but a little paler. Claw — Chartreuse green (HCC, page 90, shade 663/3) with shades of white on the lateral edges.

*Surface.* — Upper face: smooth, hairless, satiny; lower face: smooth, hairless, satiny.

*Consistency.*—Average thickness, leathery, resistant.

Reproductive organs: Stamens: on average 8–10 around the ovary, inserted between the petals, or even bunched on the claws of the petals. Long filaments of about 30–35 mm., thin, erect, white, cerous. Anthers almost always present, small, lanceolated, bilocular, yellow.

*Ovary.* — Superior, of average size, pear-shaped, averagely ribbed. Styles: generally 4, sometimes 2, tapering, with points curved over and rounded, divergent from each other, white, of average thickness. Stigmas: present on the inner surface of the styles.

Scent: Not very noticeable, sweet, spicy tones.
Resistance of flowers to transport: Very good.
Resistance of flowers to inclemency of weather: Very good.
Resistance of flowers once cut: Remarkable.
Resistance of plant to inclemency of weather: Good.
Resistance of plant to disease: Very good.
Hardiness of plant for industrial cultivation: Very good.

What is claimed is:

1. A perpetual flowering carnation of slender growth, having flowers colored Primrose yellow with shades of Chartreuse green, characterized in that the first plant of this variety was obtained by stabilizing a bud mutation ("Sport") of the yellow flowered variety of perpetual flowering hybrid called "Alice," said plant having the following unique combination of characteristics:

a. *from the physical standpoint*: a plant that grows to an average height of 100–120 cm. from the ground, while remaining erect, vertical; remarkably sturdy, with numerous flowering branches starting from close to the soil and diverging only slightly from the axis of the plant, straight, rigid, with sometimes a slight angle at the nodes; having abundant foliage, with long wide leaves over total height of plant, leaf stems slightly divergent, curved downwards in an arc or slightly bent over, sometimes forming a circle or spiral; having average to large flowers of very regular shape, regularly rounded outline, slightly scalloped and delicately indented, well developed outer petals, center of the flower averagely raised and full, central petals free, vertical, folded or curly, with the corolla colored Primrose yellow with shades of Chartreuse green and a few radial streaks tinted with white;

b. *from the physiological standpoint*: a plant that is resistant to disease, and is more than sufficiently hardy for industrial production in different types of soil; that is perpetual flowering, with many flowers, which are resistant to inclemency of weather and to discoloration from sunlight, withstand transport and packing well, which last well after being cut and are eminently suited for commerce and export; and the flowers and other parts of the plant being suitable for reproduction by agamic means.

No references cited.

R. E. BAGWILL, Primary Examiner.